(12) United States Patent
Wang

(10) Patent No.: US 6,719,774 B1
(45) Date of Patent: Apr. 13, 2004

(54) METHOD FOR FORMING LOW PROFILE BALLOON AND LOW PROFILE BALLOON FOR USE WITH A CATHETER

(75) Inventor: Chicheng Wang, Sunnyvale, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/471,199

(22) Filed: Dec. 23, 1999

(51) Int. Cl.$^7$ .............................................. A61M 29/00
(52) U.S. Cl. ............. 606/194; 604/103.07; 604/103.08; 604/103.06
(58) Field of Search ................... 604/103.06–103.08, 604/103, 96.01, 104, 509, 101.01–101.02, 101.05, 912, 915–920; 606/191, 194

(56) References Cited

U.S. PATENT DOCUMENTS

| | | | |
|---|---|---|---|
| 3,694,280 A | 9/1972 | Hoef | 156/73 |
| 3,918,216 A | 11/1975 | Best et al. | 51/283 |
| 4,321,226 A | 3/1982 | Markling | 264/139 |
| 4,384,942 A | 5/1983 | Glowacki | 204/129.46 |
| 4,490,421 A | 12/1984 | Levy | 428/35 |
| 4,551,292 A | 11/1985 | Fletcher et al. | 264/139 |
| 4,636,346 A | 1/1987 | Gold et al. | 264/139 |
| 4,952,357 A | 8/1990 | Euteneuer | 264/129 |
| 5,215,614 A | 6/1993 | Wijkamp et al. | 156/153 |
| 5,240,537 A | 8/1993 | Bodicky | 156/244.13 |
| 5,254,091 A * | 10/1993 | Aliahmad et al. | 604/103.06 |
| 5,320,634 A | 6/1994 | Vigil et al. | |
| 5,334,146 A * | 8/1994 | Ozasa | 604/103.06 |
| 5,370,618 A | 12/1994 | Leonhardt | |
| 5,378,237 A | 1/1995 | Boussignac et al. | |
| 5,425,903 A | 6/1995 | Sloane, Jr. et al. | 264/22 |
| 5,456,666 A | 10/1995 | Campbell et al. | |
| 5,556,383 A * | 9/1996 | Wang et al. | 604/103.11 |
| 5,571,087 A | 11/1996 | Ressemann et al. | |
| 5,587,125 A | 12/1996 | Roychowdhury | |
| 5,653,230 A | 8/1997 | Ciaglia et al. | |
| 5,797,878 A | 8/1998 | Bleam | |
| 6,045,547 A | 4/2000 | Ren et al. | |
| 6,251,094 B1 | 6/2001 | Bleam | |

* cited by examiner

*Primary Examiner*—Brian L. Casler
*Assistant Examiner*—Catherine Serke
(74) *Attorney, Agent, or Firm*—Blakely, Sokoloff, Taylor & Zafman LLP

(57) ABSTRACT

Methods for forming low profile balloons for use with a catheter by providing a polymeric tube, removing material from the outer surface of the polymeric tube around at least one of its end portions, and inflating a region of the polymeric tube between the two end portions to form the balloon. Low profile balloons having end portions with an outer diameter below 30 mils are also disclosed.

17 Claims, 3 Drawing Sheets

METHOD FOR FORMING LOW PROFILE BALLOON AND LOW PROFILE BALLOON FOR USE WITH A CATHETER

FIELD OF THE INVENTION

The present invention relates to balloon catheters in general and, more particularly, to methods for forming low profile balloons for catheters.

BACKGROUND

Balloon catheters have found widespread use for treating a variety of vascular diseases. Typically, a physician guides the catheter with a balloon thereon through a patient's vascular system and positions the balloon across a stenosis. The balloon is then inflated, stretching the vessel and/or pressing the lesion into the vessel wall to re-establish blood flow through the vessel. To treat a very tight stenosis with small opening, a low profile catheter and balloon that can fit through and across the stenosis is required. A low profile also improves the ability to navigate the catheter through tortuous vascular structures.

FIG. 1 illustrates a typical balloon catheter assembly in a pre-inflated state. The balloon catheter assembly 10 shown comprises an inner shaft 20 placed coaxially within an outer shaft 30, and a balloon 40 affixed co-axially over the inner and the outer shafts. The balloon 40 has a balloon region 42 interposed between a proximal portion 44 and a distal portion 46. The proximal portion 44 of the balloon is sealingly attached with the outer shaft 30 and the distal portion 46 with the inner shaft 20, with the balloon region 42 being folded or wrapped about the inner shaft.

The balloon 40 typically is formed of a continuous, flexible piece of non-elastomeric polymeric material. One balloon forming technique, known as balloon blowing, involves providing a polymeric tube and expanding a region of the polymeric tube under pressure to form the balloon region of the balloon. To narrow the proximal and the distal portions of the balloon, the end portions of the polymeric tube that will become the proximal and the distal portions of the balloon are "necked", or stretched, while the region of the polymeric tube that will form the balloon region of the balloon is kept the same. Necking reduces both the inner and the outer diameters of the end portions while simultaneously elongating the end portions of the polymeric tube.

Necking has its limits, however. On a molecular level, necking causes the polymer molecules to orient. As the end portions are stretched more and more, the outer diameter of the end portions become narrower and narrower, and the polymer molecules become more and more oriented. At some point, the polymer molecules will become so oriented that the end portions of the polymeric tube lose their flexibility, and can be stretched no further and will break instead. At this point, the polymeric tube is no longer useful for forming into a balloon. Necking alone often can not reduce the outer diameter of the proximal and the distal portions of the balloon sufficiently to produce a low profile catheter capable of maneuvering through very tight vascular structures or through very tight stenoses.

SUMMARY OF THE INVENTION

The present invention describes methods of forming a low profile balloon that can be used with a catheter. The methods involve providing a polymeric tube, removing material from the outer surface of the polymeric tube around at least one of the end portions of the polymeric tube, and inflating a region of the polymeric tube to form the balloon. The end portions of the polymeric tube optionally may be necked prior to the removal of material from the outer surface thereof. Material from the outer surface of the polymeric tube may be removed by various means. In one embodiment, the material is removed using a grinding wheel. In another embodiment, the material is removed using a laser. In yet another embodiment, the material is removed using a lathe.

DETAILED DESCRIPTION

Methods for forming low profile catheter balloons are disclosed herein. The methods and low profile catheter balloons in accordance with the present invention will be described below in connection with the Figures. The Figures and the discussion below are not intended to limit the scope of the present invention.

Low profile catheter balloons are formed from a polymeric tube by removing material from the outer surface around at least one of the end portions of the polymeric tube. Other methods of forming balloons stretch, or neck, the end portions of the polymeric tube to reduce the diameter at the end portions. As discussed above, necking often fails to achieve a sufficiently low profile at the end portions, and often results in rendering the polymeric tube useless for forming into a catheter balloon.

Figure 1:
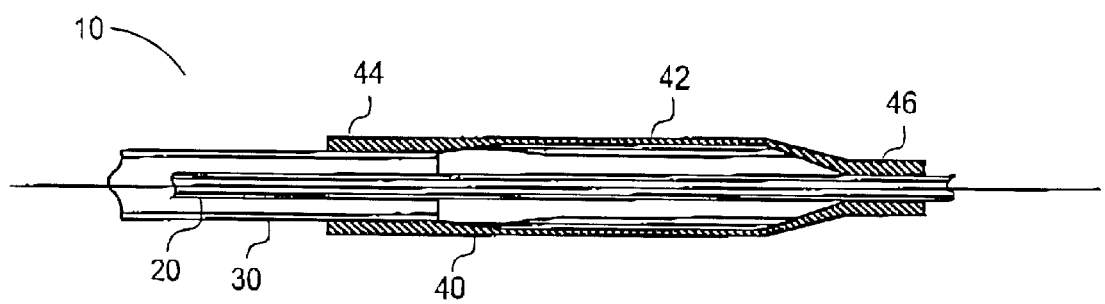
FIG. 1 shows a longitudinal, cross-sectional view of a typical balloon catheter.
Figure 2:
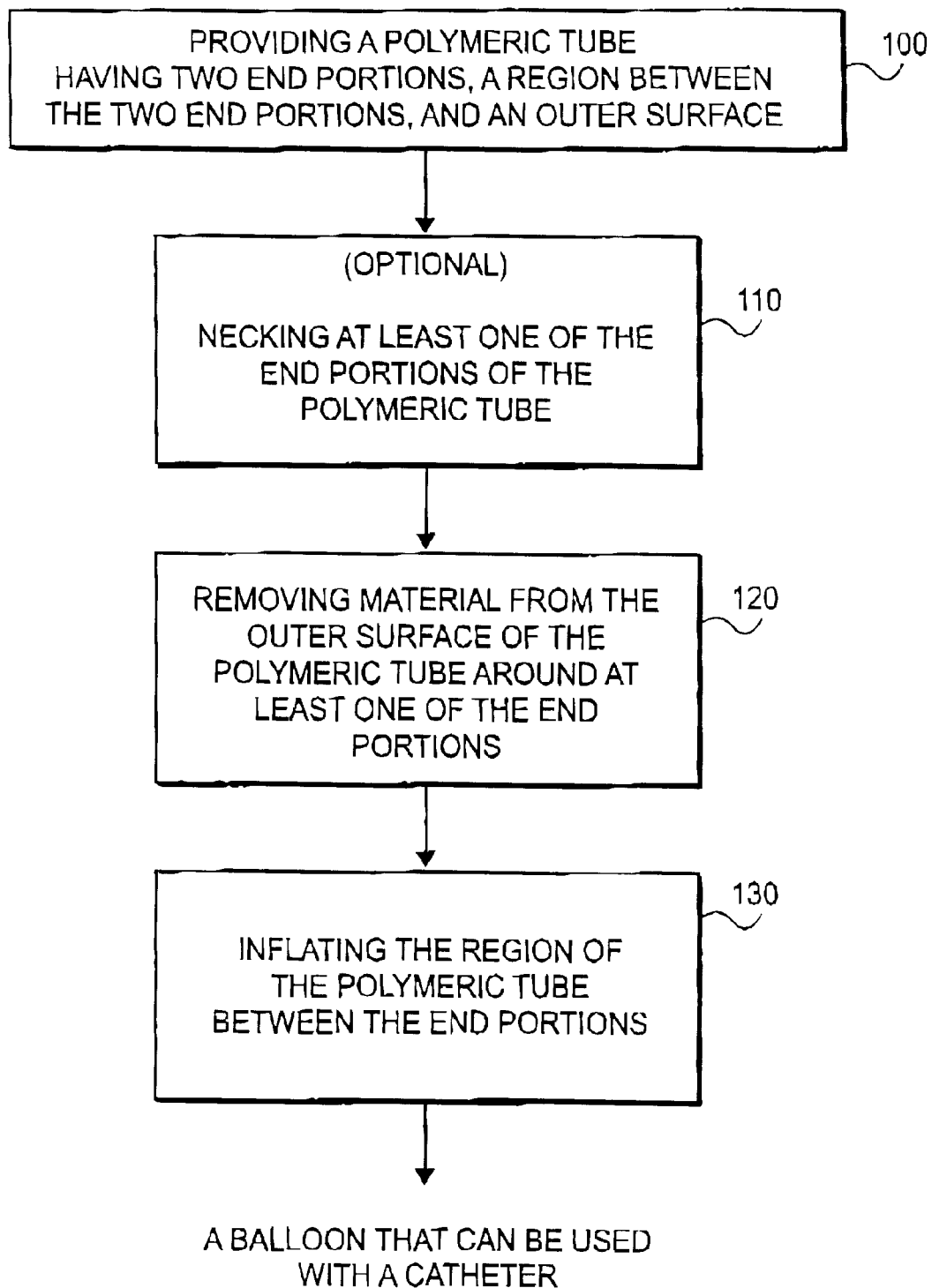
FIG. 2 is a flow chart of one embodiment of a balloon formation method in accordance with the present invention.

FIG. 2 is a flow chart of a general balloon formation method in accordance with the present invention. The method begins at 100 by providing a polymeric tube having two end portions, a region between the two end portions, and an outer surface. At least one of the end portions of the polymeric tube may be necked in an optional step 110. Material is removed from the outer surface of the polymeric tube around either or both of the end portions at 120. The region of the polymeric tube between the two end portions is inflated at 130, forming a low profile balloon that can be used with a catheter.

FIGS. 3A through 3D shows a polymeric tube after each of the steps shown in the flow chart of FIG. 2. As discussed above, the method begins by providing a polymeric tube 200 having an outer surface 205 and a region 210 between two end portions 220, 230. The polymeric tube 200 starts off having a first inner diameter ($ID_1$) and a first outer diameter ($OD_1$). It should be noted that the methods of the present invention may be implemented with polymeric tubes having any value of $ID_1$ and $OD_1$.

The polymeric tube is made of a solid polymer. In one embodiment, the polymeric tube is made of a solid polymer such as a polyamide, a polyethylene, a polyurethane, a polyethylene terephthalate (PET), and co-polymers thereof. In another embodiment, the polymeric tube comprises a polyamide-polyether block co-polymer, such as PEBAX®.

Figure 3A:
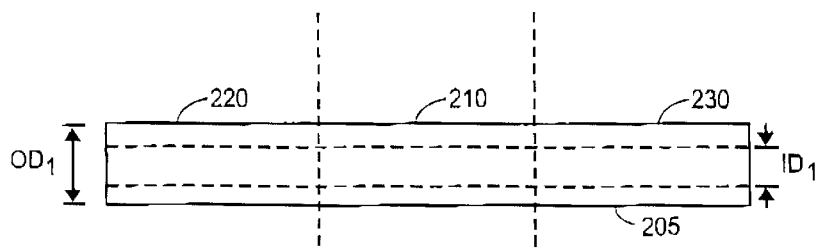
FIGS. 3A–3D depicts a polymeric tube after each of the steps in the flow chart of FIG. 2.
Figure 3B:
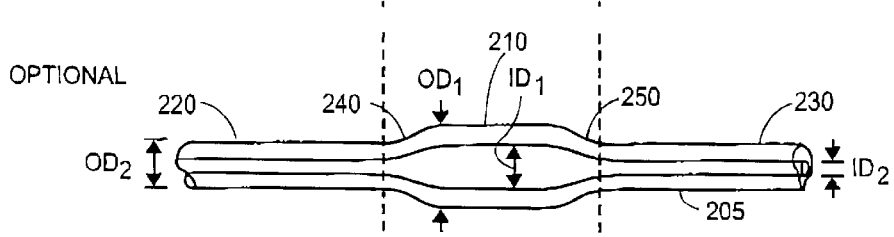
Figure 3C:
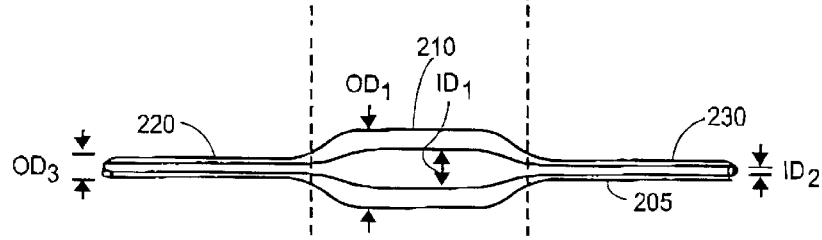

FIG. 3B shows the polymeric tube 200 after an optional necking step, in which at least one of the end portions 220, 230 of the polymeric tube 200 is necked, or stretched. In the embodiment shown in FIG. 3B, both end portions 220, 230 have been necked. Necking elongates the end portions 220, 230 of the polymeric tube and reduces the outer diameter at the end portions 220, 230 from $OD_1$ to a second outer diameter, $OD_2$, and the inner diameter from $ID_1$ to a second inner diameter, $ID_2$. The inner and outer diameters at the region 210 between the two end portions remain at $ID_1$ and $OD_1$, respectively, however. It should be noted that, typically, necking does not appreciably remove material from or reduce the mass of the polymeric tube.

The end portions of the polymeric tube need not be necked. If $ID_1$ is less than a desired outer diameter ($OD_3$) at the end portion of the balloon, then necking is purely optional and may be omitted. If, however, $ID_1$ is greater than or equal to $OD_3$, then necking becomes necessary in order to reduce the inner diameter at the end portion to less than $OD_3$.

For purposes of the present invention, necking may be achieved by any of various techniques. In one embodiment, the end portions are necked by stretching the ends of the polymeric tube in opposite directions. In another embodiment, the end portions are necked by inserting one end of the polymeric tube into a die and passing the die over the end portion (or pulling the end portion through the die) until the region is reached; then this process is repeated from the other end. Regardless of the particular technique used, necking will produce transition regions 240, 250 between the region 210 and the end portions 220, 230 of the polymeric tube.

Figure 4A:
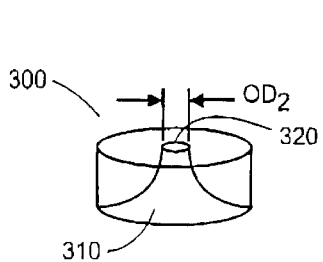
FIGS. 4A–4C show three embodiments of a die that may be used in an optional necking step in accordance with a method of the present invention.
Figure 4B:
Figure 4C:

FIGS. 4A, 4B and 4C illustrate three embodiments of a die that may be used to neck the end portions of the polymeric tube. As shown in FIG. 4A, the die 300 has a first opening 310 and a second opening 320. The first opening has a diameter large enough to accommodate the polymer tube having an outer diameter of $OD_1$. The second opening has a diameter equal to $OD_2$. One end of the polymeric tube is inserted through the first opening 310. As the die is passed over the end portion of the polymeric tube (or the end portion is pulled through the die) and the end portion exits through the second opening 320, the die elongates and reduces the outer and inner diameter of the end portion. The die is passed over the end portion (or the end portion is pulled through the die) until the region is reached, at which point the polymeric tube is removed from the die and the process repeated from the other end of the polymeric tube.

When a die is used to neck the end portions, the die determines what shape and angle the transition regions 240, 250 will have. For purposes of the present invention, the transition regions 240, 250 may have various shapes and various angles. For example, the die embodiment depicted in FIG. 4A will produce convexly curved transition regions like those shown in FIG. 3B at 240 and 250. The die embodiment depicted in FIG. 4B will produce straight angled transition regions, and the die embodiment depicted in FIG. 4C will produce concavely curved transition regions.

In one embodiment, a wire may be inserted through an end portion of the polymeric tube before necking to control the inner diameter of the end portion. The wire can have a diameter equal to a desired inner diameter for the end portion.

The outer diameter of at least one of the end portions 220, 230 is reduced further by removing material from the outer surface 205 of the polymeric tube 200 around the end portion until the desired outer diameter, $OD_3$, is achieved. In the embodiment shown in FIG. 3C, the outer diameter of both end portions 220, 230 has been reduced to $OD_3$. Typically, $OD_3$ is between about 70 mils and about 26 mils; preferably, $OD_3$ is less than about 30 mils. The step of removing material from the outer surface 205 does not affect the inner diameter at the end portions, which remains at $ID_2$. $OD_3$ is preferably about 10 mils larger than $ID_2$. Outer diameters in this range, particularly those below 30 mils, are difficult to achieve using techniques currently known in the art.

Figure 5:
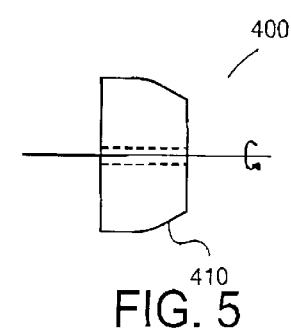
FIG. 5 shows a side-view of an embodiment of a grinding wheel that may be used in accordance with a method of the present invention.

For purposes of the present invention, the material from the outer surface 205 of the polymeric tube 200 may be removed by a variety of techniques. In one embodiment, the material is removed by a grinding wheel. The grinding wheel may be a part of a centerless grinding apparatus or any other type of grinding apparatus. FIG. 5 shows a side-view of one embodiment of a grinding wheel 400 that may be used in accordance with the present invention. Advantageously, the grinding wheel is shaped 410 to match the shape and angle of the transition regions 240, 250. Distorting the shape and angle of the transition region can diminish the mechanical integrity of the region. By shaping the grinding wheel, material from the end portions of the polymer tube may be removed without distorting the transition regions.

In another embodiment, the material is removed using a laser. Any laser can be used, such as an excimer laser or a $CO_2$ laser, and the laser may be either pulsed or continuous. The laser removes the material through ablation or by cutting.

In yet another embodiment, the material is removed using a lathe. Using a lathe, the amount of material that is removed from the end portions of the polymer tube can be readily controlled and the shape of the transition region easily maintained. The cutting edge of the lathe tool may have various shapes and/or various angles to be useful in accordance with the present invention.

Figure 3D:
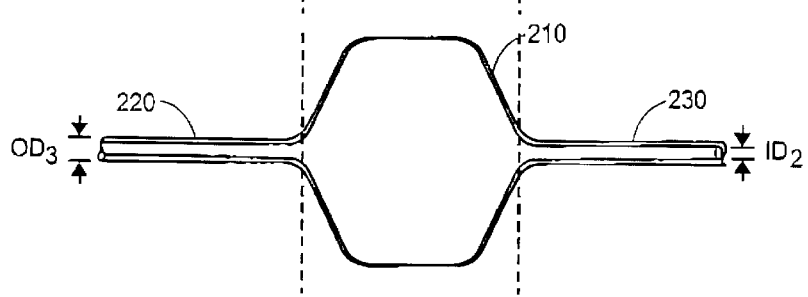

After removing material from the outer surface of the polymeric tube around at least one of the end portions, the region 210 between the two end portions is inflated to form a balloon 275 that can be used with a catheter, as shown in FIG. 3D. In one embodiment, inflating the region is achieved by placing the region within a mold that has an inner surface corresponding to a desired shape of the balloon in an inflated state. The region is inflated under pressure so that it conforms to the inner surface of the mold and acquires the desired balloon shape. In one embodiment, heat is applied to the region to soften the material of the region so it can be more readily inflated.

A catheter assembly comprising a balloon formed by the methods of the present invention can be fabricated by conventional techniques and used in accordance with accepted medical procedures.

Numerous variations, modifications and improvements to the embodiments described above may be made in accordance with the present invention. For example, the embodiments described above show both end portions having the same inner and outer diameter; however, this need not be the case. The end portions may have a different inner and/or outer diameter after either or both necking and removing material from the outer surface around the end portions.

Also, the embodiments described above show material being removed from the outer surface around at least one of the end portions before the region between the end portions is inflated. However, the order of these steps may be reversed and the material removed from the outer surface around at least one of the end portions after the region is inflated.

Those of ordinary skill in the art will recognize that other variations, modifications, and improvements also may be made to the embodiments described above and still fall within the scope of the invention as claimed.

What is claimed is:

1. A balloon for use with a catheter, the balloon comprising:

an outer surface comprising a balloon material;

two end portions having an inner diameter and an outer diameter; and a region between the two end portions, wherein the region has two transition portions leading to the two end portions, and wherein the outer surface beyond at least one of the two transition portions and near at least one of the end portions has less balloon material than the outer surface near the region between the two end portions.

2. The balloon as described in claim 1, wherein at least one of the end portions has an inner diameter that is about 10 mils smaller than the outer diameter.

3. The balloon as described in claim 1, wherein the outer diameter of the end portions is between about 70 mils and about 26 mils.

4. The balloon as described in claim 1, wherein the balloon comprises a solid polymer selected from the group consisting of: a polyamide, a polyethylene, a polyurethane, a polyethylene terephthalate, and co-polymers thereof.

5. The balloon as described in claim 1, wherein the balloon comprises a polyamide-polyether block co-polymer.

6. The balloon as described in claim 1, wherein the outer diameter of the outer surface near the at least one of the end portions being between about 70 mils and about 26 mils.

7. A balloon for use with a catheter, the balloon comprising:

an outer surface comprising a balloon material;

two end portions having an inner diameter and an outer diameter; and a region between the two end portions, wherein the region has two transition portions leading to the two end portions, and wherein the outer surface beyond at least one of the two transition portions and near at least one of the end portions has less balloon material than the outer surface near the region between the two end portions, and the outer diameter of the outer surface near the at least one of the end portions being less than about 30 mils.

8. The balloon as described in claim 7, wherein at least one of the end portions has an inner diameter that is about 10 mils smaller than the outer diameter.

9. The balloon as described in claim 7, wherein the outer diameter of the end portions is less than about 30 mils.

10. The balloon as described in claim 7, wherein the balloon comprises a solid polymer selected from the group consisting of: a polyamide, a polyethylene, a polyurethane, a polyethylene terephthalate, and co-polymers thereof.

11. The balloon as described in claim 7, wherein the balloon comprises a polyamide-polyether block co-polymer.

12. A balloon for use with a catheter, the balloon comprising:

an outer surface comprising a balloon material;

two end portions, at least one of end portions having a first inner diameter and a first outer diameter; and a region between the two end portions, wherein the region has two transition portions leading to the two end portions, wherein at least a portion of the region has a second inner diameter and a second outer diameter, and wherein the difference between the first inner diameter and the first outer diameter beyond at least one of the two transition portions is less than the difference between the second inner diameter and the second outer diameter.

13. The balloon as described in claim 12, wherein the outer surface near at least one of the end portions has less balloon material than the outer surface near the region between the two end portions.

14. The balloon as described in claim 12, wherein the difference between the first inner diameter and the first outer diameter of at least one of the end portions is about 10 mils.

15. The balloon as described in claim 12, wherein the first outer diameter being less than about 30 mils.

16. The balloon as described in claim 12, wherein the balloon comprises a solid polymer selected from the group consisting of: a polyamide, a polyethylene, a polyurethane, a polyethylene terephthalate, and co-polymers thereof.

17. The balloon as described in claim 12, wherein the balloon comprises a polyamide-polyether block co-polymer.

* * * * *